United States Patent
Fuhr et al.

(10) Patent No.: US 9,310,119 B2
(45) Date of Patent: Apr. 12, 2016

(54) COOLING SYSTEM, ESPECIALLY FOR CRYOPRESERVING BIOLOGICAL SAMPLES, COMPRISING DEVICES FOR USE IN CASE OF AN EMERGENCY

(75) Inventors: Guenter R. Fuhr, Berlin (DE); Heiko Zimmermann, Frankfurt am Main (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 258 days.

(21) Appl. No.: 13/983,055

(22) PCT Filed: Feb. 1, 2012

(86) PCT No.: PCT/EP2012/000450
§ 371 (c)(1),
(2), (4) Date: Jul. 31, 2013

(87) PCT Pub. No.: WO2012/104079
PCT Pub. Date: Aug. 9, 2012

(65) Prior Publication Data
US 2013/0305746 A1 Nov. 21, 2013

(30) Foreign Application Priority Data
Feb. 2, 2011 (DE) .......................... 10 2011 010 120

(51) Int. Cl.
*F25D 23/12* (2006.01)
*F25D 3/10* (2006.01)
*A01N 1/02* (2006.01)
(Continued)

(52) U.S. Cl.
CPC ................ *F25D 3/10* (2013.01); *A01N 1/0252* (2013.01); *A01N 1/0257* (2013.01); *F25D 29/006* (2013.01); *F25D 3/102* (2013.01); *F25D 13/00* (2013.01)

(58) Field of Classification Search
CPC ...... F25D 17/005; F25D 17/08; F25D 29/001; A61G 3/001
See application file for complete search history.

(56) References Cited

U.S. PATENT DOCUMENTS 3,127,755 A 4/1964 Hemery
3,287,925 A 11/1966 Kane et al.
(Continued)

FOREIGN PATENT DOCUMENTS

DE 2019882 11/1971
DE 3028707 A1 6/1981
(Continued)

OTHER PUBLICATIONS

International Search Report for PCT/EP2012/000450 dated Sep. 6, 2012.

*Primary Examiner* — Allen Flanigan
*Assistant Examiner* — Filip Zec
(74) *Attorney, Agent, or Firm* — Caesar Rivise, PC

(57) ABSTRACT

A cooling system (1), especially for cryopreserving biological samples (2), comprises a cooling chamber (100) delimited by a bottom area (110), side walls (120), and a top area (130), and a cooling device (200) for cooling the cooling chamber (100) using liquid nitrogen (220). At least one of the side walls (120) includes at least one predetermined wall element (125) which is a portion of at least one of the side walls and can be moved relative to the associated side wall (120) in such a way that a wall opening can be formed in said side wall (120). Methods for operating the cooling system (1) in case of an emergency are also described.

17 Claims, 8 Drawing Sheets

(51) Int. Cl.
*F25D 29/00* (2006.01)
*F25D 13/00* (2006.01)

(56) References Cited

U.S. PATENT DOCUMENTS

| | | | |
|---|---|---|---|
| 3,385,073 A | | 5/1968 | Snelling |
| 4,060,400 A | | 11/1977 | Williams |
| 4,367,630 A | * | 1/1983 | Bernard ................ A23B 4/062 62/63 |
| 4,576,010 A | | 3/1986 | Windecker |
| 4,599,871 A | * | 7/1986 | Fredrixon ............... F25D 13/04 62/378 |
| 4,989,417 A | * | 2/1991 | Markiewicz ............ F25D 13/04 62/407 |
| 5,150,585 A | * | 9/1992 | Markiewicz .............. F02C 1/10 62/402 |
| 5,327,731 A | | 7/1994 | Markiewicz |
| 5,630,296 A | | 5/1997 | Kendall, Jr. |
| 6,415,453 B1 | | 7/2002 | Anderson et al. |
| 2003/0012639 A1 | | 1/2003 | Seitz |
| 2006/0041994 A1 | | 3/2006 | Germain et al. |
| 2006/0156753 A1 | | 7/2006 | Fuhr et al. |
| 2008/0104976 A1 | * | 5/2008 | Guglielmetti ......... F25D 29/001 62/127 |
| 2009/0273265 A1 | * | 11/2009 | Aragon ................... F25D 3/125 312/405 |

FOREIGN PATENT DOCUMENTS

| | | |
|---|---|---|
| DE | 3441091 A1 | 5/1986 |
| DE | 19716913 A1 | 11/1998 |
| DE | 102007015390 A1 | 10/2008 |
| EP | 1639892 A1 | 3/2006 |
| EP | 1252417 B1 | 11/2008 |
| GB | 1305706 | 2/1973 |
| WO | 2005010499 A2 | 2/2005 |
| WO | 2008116723 A1 | 10/2008 |

* cited by examiner

COOLING SYSTEM, ESPECIALLY FOR CRYOPRESERVING BIOLOGICAL SAMPLES, COMPRISING DEVICES FOR USE IN CASE OF AN EMERGENCY

BACKGROUND OF THE INVENTION

The invention concerns a cooling system, in particular for cryopreservation of biological samples, which has a cooling chamber cooled with liquid nitrogen ($LN_2$). The invention furthermore concerns methods for operating the cooling system in case of an average (emergency, accident). Applications of the invention are given in long-term storage of samples in the cooled state, in particular for cryopreservation of biological samples.

It is known to store biological samples for the purpose of preservation in the frozen state in a cooling system, e.g. in a cryobank (cryopreservation). Cryobanks are typically operated at temperatures below −80° C., in particular at a temperature below the recrystallization temperature of water ice (−138° C.). They contain a cooling medium reservoir with liquid nitrogen (temperature: about −195° C.) and a plurality of individual tanks (so-called cryotanks, mostly Dewar flasks made of double-walled steel) with the size ranging from a few liters up to about 2 or 3 cubic meters. The cryotanks stand in rooms at normal temperature (room temperature) and are supplied with said liquid nitrogen from the cooling medium reservoir. In the cryotanks, boxes in which tubes, bags or other closed receptacles with the samples (e.g. liquids, cells, cell constituents, serums, blood, cell suspensions, pieces of tissue or the like) are stored are arranged in shelves. The samples can be fully arranged in the liquid nitrogen. To prevent contamination of samples by the liquid nitrogen, the samples are, however, mostly stored in a cool gaseous phase in the vapour of the liquid nitrogen at approximately −145° C. This gaseous phase is formed above a nitrogen lake on the floor of the cryotank.

The conventional cryotanks have high operating safety in the normal operation mode. As long as the supply with the liquid nitrogen is maintained, safe storage of the samples is guaranteed. However, if the supply of nitrogen is interrupted or the vacuum breaches in the Dewar flask in the case of an average, the samples must be transferred to another cryotank. During this transfer, there is high risk, especially if many cryotanks are concerned, that samples are undesirably warmed up. Even more critical are situations of average resulting from a fire or inrush of water.

Conventional cryobanks with individual cryotanks have, however, disadvantages when large sample quantities, such as ten thousand up to a million or more samples, are to be cryopreserved. Limitations occur as to the effectiveness of the cryotank operation for the provision of constant cooling conditions and for the automation when operating the cryobank, in particular the sample handling. To overcome these limitations, there is the interest to replace the conventional cryotanks by larger storage devices as are used for instance for storage of food. Cooling chambers are known, which allow effective storage of food and automation. However, due to their operating temperature in a range above −50° C., the conventional cooling chambers are not suitable for long-term cryopreservation of biological samples.

An extended cooling system, which is suitable for the cryopreservation of biological samples is described by the inventors of the present invention in a further patent application (not yet published at the priority date of the present invention). The cooling system comprises a cooling chamber, which is delimited by a floor area, side walls and a ceiling area, and a cooling device, which is provided for cooling of the cooling chamber with liquid nitrogen. Even if cryopreservation in an expanded cooling chamber (cold room) is advantageous with respect to the effectiveness of the cooling and the automation of the sample handling, there are, in contrast to conventional cryotanks, higher risks in case of an average. For example, in the event of failure of the cooling device, the samples cannot be removed as rapidly from the cooling chamber as from a cryotank. Particular measures for removal of refrigerated goods are neither known for the conventional cooling chambers for storage of food.

There is a further problem when operating cooling chambers with respect to the protection of operators, which stay in the cooling chamber. No measures are known for the protection of an operator in case of an average where the operator is exposed in the cooling chamber to life-threatening conditions.

EP 1 252 471 B1, DE 10 2007 015 390 A1, U.S. Pat. No. 4,576,010 A, U.S. Pat. No. 4,060,400 A, U.S. Pat. No. 3,287, 925 A, U.S. Pat. No. 3,385,073 A and U.S. Pat. No. 3,127,755 A describe cooling vehicles with liquid nitrogen cooling, whose cooling chamber respectively has a door opening with a door allowing access to the refrigerated goods. These cooling vehicles are unpractical for cryopreservation of biological samples, since the door opening allows the inflow of ambient air, which results in icing of the interior of the cooling chamber.

The objective of the invention is to provide an improved cooling system, in particular for cryopreservation of biological samples, which allows to overcome disadvantages and limitations of conventional cooling systems. The cooling system should in particular allow protection of cryopreserved samples and/or of an operator in case of an average allow. The objective of the invention is also to provide an improved method for operation of a cooling system, in particular for cryopreservation of biological samples, with which disadvantages and limitations of conventional methods are overcome in case of an average.

These objectives are solved by cooling systems and methods for operating the cooling systems having the features of the invention.

DESCRIPTION OF INVENTION

According to a first aspect of the invention, a cooling system, in particular for cryopreservation of biological samples, is provided, which has a cooling chamber and a cooling device, which are adapted for cooling of the cooling chamber using liquid nitrogen. The cooling chamber is generally a room enclosed by a floor area, side walls and a ceiling area, which is cooled in its entirety with the cooling device and is adapted for accommodating the samples to be preserved. The cooling chamber is preferably arranged stationary and immovable. It is particularly preferably configured to be directly cooled by liquid nitrogen or the vapour of the liquid nitrogen. According to the invention, at least one of the side walls contains at least one wall element, which can be moved relative to the respective side wall. The at least one wall element is configured in such a way that a wall opening can be formed in the side wall by a movement of the wall element relative to the side wall. The wall element is a part of the side wall. A movement of the wall element device in particular that the wall element can be moved from a closed state, in which the side wall is completely closed with the wall element, to an opened state in which the side wall is interrupted at the wall opening. Advantageously, the at least one wall element allows an emergency opening of the cooling chamber for rapid removal of samples (evacuation) and/or of persons from the cooling chamber in case of an average.

The wall element can be moved instantaneously, that is without any delay affecting the state of the cryopreserved samples, relative to the side wall in order to form the wall opening. In distinction to the conventional cryotank, for which sample access is provided only from above through a tank lid, the at least one wall element provided for according to the invention allows side access to samples in the cooling chamber. This can advantageously considerably accelerate the evacuation of samples. In distinction to a conventional cooling chamber for food, the at least one wall element provided for according to the invention does not represent a door provided for regular sample access, but rather a subregion of the wall. This advantageously prevents the formation of undesirable heat sink in the cooling chamber.

According to a second aspect of the invention, a method for operating the cooling system according to the above first aspect of the invention is provided for which, after detection of a state of average in the cooling system, action is done on an operator and/or samples in the cooling chamber until their environmental conditions correspond to a desired normal state. The state of average is given when the operator and/or the samples in the cooling chamber are exposed to operating conditions, which differ from a predetermined normal state. According to the invention, the state of the operator and/or of the samples and of the use of individual or several protective measures of the cooling system for the case of an average are changed until the environmental conditions of the operator and/or the samples correspond to the normal state.

In the case of the operator, the operating conditions comprise, for example, the temperature and/or the oxygen content inside a protective suit of the operator and/or the operability of mechanical components of the protective suit, such as joints. The normal state is characterized for the operator, for example, by a temperature above 0° C. and the provision of breathable air in the direct environment of the operator, and for the protective suit by the mobility of the joints.

With respect to the samples, the operating conditions comprise the temperature and/or the existence of undesirable substances in the cooling chamber. The normal state is characterized for the samples, for example, by a temperature below −138° C. and/or the dryness of the atmosphere in the cooling chamber.

According to the invention, the cooling chamber is dimensioned such that at least one operator can stay and move in the cooling chamber. The internal volume of the cooling chamber is selected such that the at least one operator completely fits in the cooling chamber and can stand and/or walk therein. Preferably, the internal volume is equal to at least 10 $m^3$, in particular at least 100 $m^3$, such as at least 500 $m^3$, or even 1000 $m^3$ or more.

The cooling chamber of the cooling system according to the invention is adapted for accommodating a sample receiving device. Any holding structure, which is suitable for accommodating samples, in particular of sample containers with biological samples, can be used as the sample receiving device. Sample containers comprise e.g. test tubes, tubelets, capillaries, so-called "straws", bags or other closed receptacles. The sample receiving device may be arranged permanently in the cooling chamber (in particular fixed) or is at least in parts releasable. According to the invention, the cooling chamber is preferably dimensioned such that the operator can stay and move in the cooling chamber provided with the sample receiving device.

According to a preferred embodiment of the invention, the at least one side wall and the at least one wall element, which is provided for in the respective side wall, has the same structure in a thickness direction of the side wall. The wall element forms a wall module, which is connected with the surrounding side wall through shape fitting or via a predetermined breaking point. The modular structure of the side wall with the wall element has the advantage that the thermal properties along the side wall are substantially constant, so that formation of a heat sink is prevented.

According to a further advantageous embodiment of the invention, the at least one wall element is perpendicularly shiftable relative to the surface extension of the respective side wall. The wall element can be moved in a direction, which is parallel to the thickness direction of the side wall. In this case, the wall opening can be created in a particularly easy manner in such a way that the wall element is shifted from the outside to the interior of the cooling chamber or from inside to the environment of the cooling system.

It would furthermore be advantageous that the wall element can be moved manually, in particular shifted manually relative to the side wall. In this case, a human operator can create the wall opening using his physical strength. The use of additional mechanical tools is not mandatory.

Particularly preferred is a variant of the invention for which the wall element can be completely separated from the side wall. This allows simplified access to the wall opening from both sides of the respective side wall.

The evacuation of the cooling chamber can be advantageously simplified if at least one of the following measures are provided for with the cooling system. According to a first variant, a docking device can be provided for an evacuation container on the external side of the at least one side wall, which has the at least one wall element. The docking device is positioned on the external side of the respective side wall such that an evacuation container coupled to the docking device is arranged adjacent to the wall element resp. the wall opening in the side wall. The docking device comprises, for example, a frame, which surrounds the wall element or the wall opening on the external side of the side wall and is adapted for coupling the evacuation container. Preferably, the docking device is configured for a thermally insulated and gas-tight connection of the cooling chamber with the coupled evacuation container with respect to an environment of the cooling system. Alternatively or additionally, a ramp is provided for on the external side of the at least one side wall with the at least one wall element. The ramp comprises a support, which leads from the bottom edge of the wall element or the wall opening in the side wall to a floor in the environment of the cooling system. Evacuation of samples from the cooling chamber is advantageously simplified by the ramp.

According to a further feature of the invention, a protection device with which a local protective atmosphere can be created in the cooling chamber in an environment of an operator is provided in the cooling chamber. The cooling system provided with the protection device in the cooling chamber represents a preferred embodiment of the cooling system according to the invention in accordance with the above first aspect. The protection device can, however, be provided for even for a cooling system with a cooling chamber and a cooling device for cooling of the cooling chamber with liquid nitrogen, without the need that at least one of the side walls of the cooling chamber is provided with the wall element. In other words, the cooling system with the protection device provided for in the cooling chamber represents an independent subject-matter of the invention. Advantageously, the protection device allows that an operator can be protected against life-threatening environmental conditions, in particular against undercooling or lack of oxygen in the case of an average.

According to an advantageous variant, the protection device comprises a hood (cover), which is movable in the cooling chamber and can be coupled with an external ventilation system. The interior of the hood can be impinged with warmed-up air with the external ventilation system. The hood is preferably made of a material, which is flexible at the operating temperature in the cooling chamber, such as a metal foil. According to a further variant, the protection device comprises movable partition walls, which are shiftable in the interior of the cooling chamber, and with which a chamber can be delimited from the rest of the cooling chamber. In this case too, an external ventilation system is provided for with which the interior of the chamber can be impinged with warmed-up air. In case of an average, an operator in the cooling chamber can get help by the operator being covered with the hood or the chamber with the shiftable partition walls being formed around the operator and the interior of the hood or the chamber being impinged with warmed-up air.

According to a further variant, the protection device can be provided with an insulating mat, for example made of a plastic material, with which the operator can be thermally insulated against the floor area.

According to a further advantageous feature of the invention, the cooling chamber can be provided with an alarm device, which is adapted for generating an alarm in reaction to any unauthorized access to the interior of the cooling chamber. This can advantageously simplify protection of the samples.

Average in a cooling system according to the invention can also occur when the conditions undesirably change in the environment of the cooling system. For example, undesirable impingement of the cooling system with water from below or from above can occur. In order to protect the samples in this case, the cooling system is provided with a lifting device and/or with an outer shell device. The lifting device and the shell device represent features of preferred embodiments of the cooling system according to the above first aspect, but can also be provided for on a cooling system with a cooling chamber and a cooling device working with liquid nitrogen for which none of the side walls is adapted for the formation of a wall opening by device of a variable wall element. In other words, the cooling systems provided with the lifting device and/or the shell device represent independent subject-matters of the invention.

The lifting device is configured to change an operating height of the cooling chamber or of its parts, e.g. individual chambers, and if necessary of the cooling device relative to a floor in the environment of the cooling system. Advantageously, the cooling chamber can be lifted above the high water level in the event of high water. Preferably, the lifting device comprises to this end a crane and/or a hydraulically operated carrier. The shell device is configured for creating a system's protective atmosphere, which surrounds the whole cooling system, in particular the whole cooling chamber. Preferably, the shell device comprises a flexible foil, for example made of plastics, by device of which the cooling system or at least the cooling chamber can be protected against water penetrating from above.

BRIEF DESCRIPTION OF THE DRAWINGS

Further advantages and details of the invention are described below with reference to the attached drawings. The figures show as follows.

Preferred embodiment of the cooling system according to the invention and of the method for operating them are described in the following with exemplary reference to a cooling system with a cooling chamber, which is dimensioned such that an operator can perform several walking steps in the cooling chamber. The realization of the invention is not restricted to the cooling chamber size exemplary shown, but is rather accordingly possible even with considerably larger cooling chambers (halls) or also with smaller cooling chambers. Embodiments of the invention are described in particular with reference to measures on the cooling system according to the invention for protection of samples or operators in case of an average and the methods for operating the cooling system in the case of an average are described as well. Details of the cryopreservation of biological samples, such as the sample preparation or the realization of certain cooling reports or the deposition of the samples together with stored sample data can be realized with the cooling system according to the invention as is known per se from the prior art.

Figure 1:
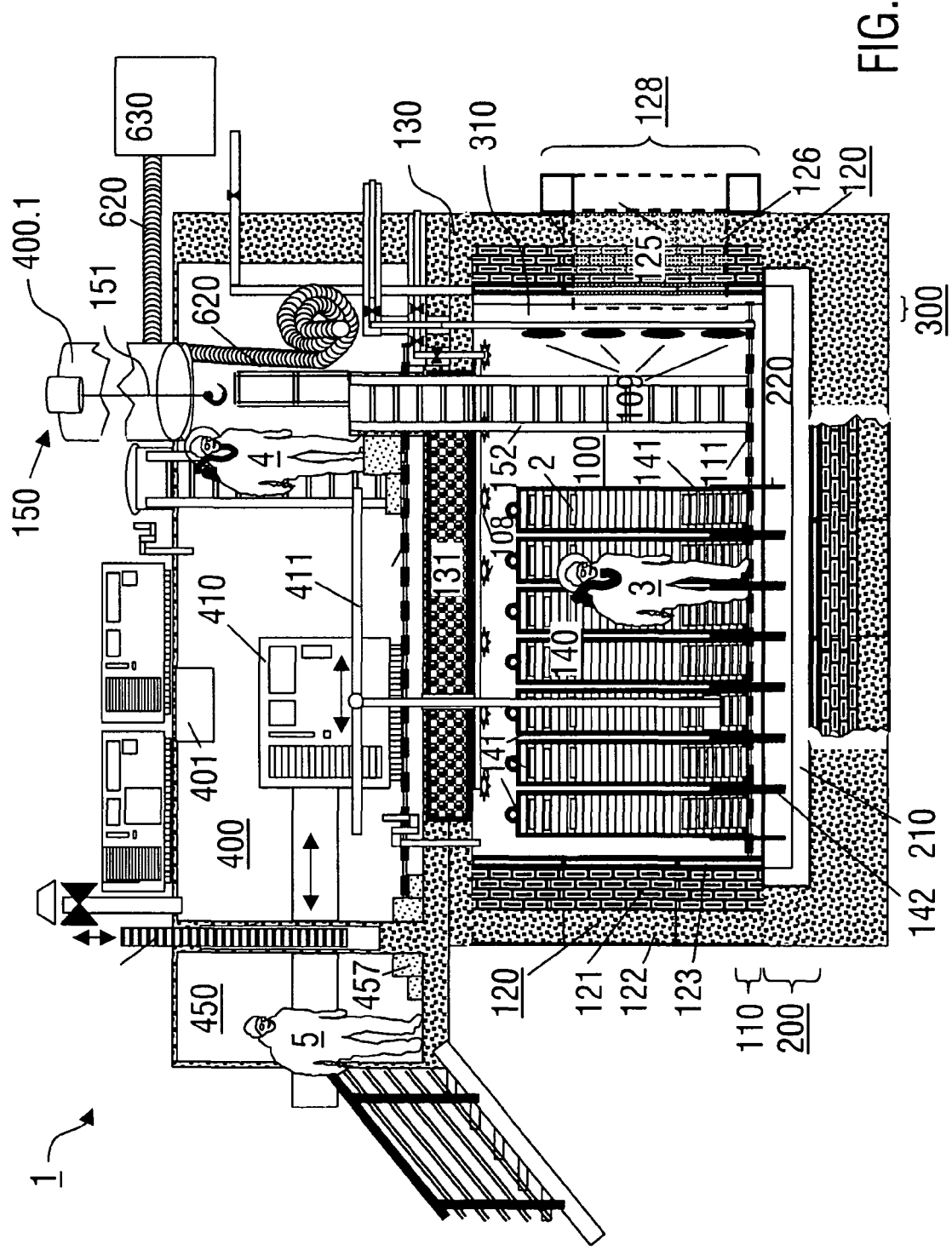
FIG. 1: a schematic cross-sectional view of a preferred embodiment of the cooling system according to the invention.

FIG. 1 shows an embodiment of the cooling system 1 according to the invention in a schematic cross-sectional view with a cooling chamber 100, a first cooling device 200, a second cooling device 300 and an operation room 400. The cooling chamber 100 is delimited downwards by a floor area 110, sidewards by side walls 120 and upwards by a ceiling area 130. The internal volume of the cooling chamber 100 is equal to e.g. 10 m·5 m·3 m. A sample receiving device 140 with shelves 141 is arranged in the cooling chamber 100, standing on the floor area 110 and adjacent to the side walls 120.

The floor area 110 comprises a platform 111, which extends over the first cooling device 200 with a trough 210. The trough 210 has a double-walled trough body with an evacuated interior and is provided on its outer side with thermal insulation. The thermal insulation has the same structure as the side walls 120. Alternatively or additionally, the trough is insulated with an infrared mirrored vacuum region. During operation of the cooling system 1, liquid nitrogen 220 is contained in the trough 210. The liquid nitrogen 220 preferably has a free surface towards the floor area 110. A nitrogen lake is formed. Filling of the trough 210 and maintaining the reservoir of liquid nitrogen 220 during operation of the cooling system 1 takes place by device of coolant supply (not shown).

The platform 111 comprises a grating, e.g. made of steel, which extends over the trough 210 and is provided with step platforms. The step platforms reduce any possible mechanical contact between an operator 3 and the platform 111, so that any heat flow from the operator 3 to the platform 111 is minimized. Since the platform 111 forms a support area for the operator 3 and also the sample receiving device, the platform 111 can be mechanically supported in the trough 210 by additional components (not shown).

The second cooling device 300 is provided for on at least one of the side walls 120, in particular on its surface pointing inwardly or embedded therein. The second cooling device 300 is configured for electric cooling. It comprises cooling elements 310, which are connected with cooling aggregates (not shown). The cooling aggregates are located outside the cooling chamber 100, preferably above it. With the second cooling device 300, it is e.g. possible to provide electric cooling down to a temperature of −150° C. According to alternative variants of the invention, the second cooling device 300 can be formed as a substitute by nitrogen cooling or cooling with liquid helium.

During operation of the cooling system 1, the first cooling device is e.g. used in the cooling chamber as the main cooling and the second cooling device as secondary safety cooling system. Alternatively, vice versa, the second cooling device can form the main cooling and the first cooling device the secondary safety cooling system.

The sample receiving device 140 comprises shelves 141 (so-called "cryo racks") in which biological samples 2 are stored in sample containers. The shelves 141 have frames made of thermally well conductive material, e.g. made of metal, which have thermal contact to the platform 111 and via thermal bridges 142 directly to the liquid nitrogen 220 in the first cooling device 200. This advantageously guarantees effective cooling up to the upper compartments of the shelves 141.

According to the invention, is contained in at least one side wall 120 at least one wall element 125, which is movable with respect to the side wall. The at least one wall element 125 is a part of the wall, which extends from the inner side up to the external side of the side wall 120 and is connected via an opening joint 126 with the surrounding side wall 120. The wall element 125 can be separated from the side wall 120 by device of a sliding movement or under the action of a hit so that a wall opening 127 (see FIG. 2) can be created. On the external side of the side wall 120 is arranged a schematically illustrated docking device 128 for a mobile evacuation container (see FIG. 2). The wall element 125 has essentially the same structure as the surrounding side wall 120. If the side wall 120 comprises e.g. several stratiform wall layers, they are likewise provided for in the wall element 125. Deviating from the illustration in FIG. 1, several wall elements 125 can be provided for the formation of wall openings in one or more of the side walls 120.

The wall element 125 is dimensioned such that the wall opening in the side wall 120 is suitable for rapid evacuation of samples 2 and/or operators 3 from the cooling chamber 100. The wall element 125 may e.g. have a circular cross-section with a diameter of e.g. 100 cm or a rectangular cross-section with a side length of 100 cm.

The side walls 120 preferably comprise several stratiform wall layers with an inner vacuum component layer 121 and an outer plastic layer 122. The vacuum component layer 121 comprises a layer of evacuated structural elements (so-called "vacuum components") and an evacuated hollow wall 123. The evacuated structural elements are formed parallelepipedic, in particular like conventional building stones or bricks for building purposes, and are made out of plastic with an evacuated or evacuatable interior. The hollow wall 123 extends over the whole side walls 120 or parts of them. In the area of the at least one wall element 125, the hollow wall 123 has a recess. The hollow wall 123 is evacuated in the normal operation mode or optionally filled with a cooling liquid. The hollow wall 123 has in particular an advantageous function for the case that one of the cooling devices fails. It may be filled from an operator-selectable external auxiliary container (not shown) with a coolant such as liquid nitrogen in order to prevent undesirable heating of the cooling chamber 100. The plastic layer 122 comprises a layer made of a polymer foam, e.g. a polyurethane foam. The thickness of the plastic layer 122 can e.g. be selected in the range of 10 cm to 1 m or also above 1 m.

The ceiling area 130 comprises a plastic layer, formed e.g. out of polymer foam, in which a ceiling opening 131 is formed. Above the ceiling opening 131 is provided the operation room 400 with a drive device 410 and mechanical control elements 411, which project into the interior of the cooling chamber 100. FIG. 1 shows by way of example a rod assembly with a shifting unit, which can be actuated with the drive device 410. Samples can be introduced into or removed from the shelves 141 of the sample receiving device with the shifting unit. Furthermore, a hood chamber 400.1 (receiving tower) is provided for in which a conveying machine 150 with a rope hoist 151 is arranged. Sample receiving devices 140, in particular the tower-like shelves 141, can be transferred in case of breakdown or during loading of the cooling chamber 100 into the hood chamber 400.1. The rope hoist 151 and a ladder 152 project from the operation room 400 through the ceiling opening 131 into the cooling chamber 100. Additionally, the operation room 400 can contain further operating devices and/or be connected to a person gate device 450.

The operation room 400 furthermore contains an alarm device 401, which is connected to sensors in the cooling chamber 100 and in the operation room 400 and, in reaction to any undesirable access to the interior of the cooling chamber 100, generates an alarm signal. Furthermore, a flexible ventilation line 620, which is connected to an external ventilation system 630, is located in the operation room 400. The ventilation line 620 can be pulled into the cooling chamber 100 in order to create there a local protective atmosphere in a hood 610 (see FIG. 5).

For inspection of the cooling chamber 100, an operator steps through the person gate device 450 into the operation room 400. Between the person gate device 450 and the operation room 400, there is a lock through which the operator 3 can access the operation room 400 via stairs 457. From the operation room 400, the inspection of the cooling chamber 100 is done through the ceiling opening 131 and by device of the ladder 152. The operator 3 wears a protective suit, which is described in a further patent application (not published on the priority date of the present invention).

Temperature sensors at different distances from the floor area 110 are provided for in the cooling chamber 100 and in the operations room 400. This allows the detection of a temperature distribution in the cooling chamber 100. If required, additional cooling with the second cooling device 300 and/or a ventilation device (not shown) in the cooling chamber 100 can take place to achieve balancing of the temperature, in particular decreasing the temperature in the upper regions of the cooling chamber 100.

Furthermore, nitrogen sprinkler system 108 is provided for in the cooling chamber 100. The nitrogen sprinkler system 108 is preferably located on the underside of the ceiling area 130. Advantageously, rapid cooling can be achieved with the nitrogen sprinkler system 108 at first use of the cooling chamber or in case of failure of a cooling device. The nitrogen sprinkler system 108 is supplied out of the coolant supply apparatus (not represented) via coolant lines.

FIG. 1 illustrates an important design of the cooling system according to the invention. All supply connections, in particular supply lines and openings, into the interior of the cooling chamber 100 exclusively occur through the ceiling area 130, i.e. from above. This leads to minimization of the heat supply. Furthermore, warmer tops can be arranged in the operation room 400 or above it for devices, which cannot operate at low temperatures. In particular, chambers with higher temperature or even with an internal heater for operation of movable parts, such as motors, can be put on top. Since gas is formed continuously from the first cooling device 200 with clear increase of volume and the cooling system 1 is designed pressure-free, i.e. not gas-tight, nitrogen continuously flows through the cooling chamber 100 from below. Also significant for the reliable operation of the cooling system 1 is that heating in the case of an average, in particular in case of failure of cooling devices, is as delayed as possible. This is in particular achieved with the thermally insulating structure of the side walls 120.

In the cooling system according to the invention for cryopreservation of biological samples with automatable cooling chambers, which are walkable in case of emergency, the case of an average is already prepared for as concerns the spatial requirements, with predetermined equipment and/or pre-defined procedures for the case of an average. In case of an average, this provides a defined procedure and the required device for quickest possible recovering of the samples as well as, if they are involved, of operators in and out of the cooling chamber concerned. For the purpose of providing better understanding of the case of an average, the normal operation mode of the cooling system according to the invention is at first described.

1. Normal Operation

During normal operation, the cooling system is in one of the operation modes, which comprise initial cooling of a cooling chamber, normal cooling, a technical check, maintenance/repair work, standby operation and closure of the sample storage in the cooling chamber.

For initial cooling, the whole cooling chamber with all installations and any pre-chambers is completely dried e.g. through heating or through gas-tight sealing of the cooling chamber with respect to the environment and introduction of dried gases. Sealing of the cooling chamber is performed, for example, using a shell device, which is described below with reference to FIG. 8. After this, liquid nitrogen is filled into the first cooling device 200. During cooling of the first cooling device 200, a high amount of dry nitrogen gas is created and presses the interior air upwards from the cooling chamber. This is continued until the first cooling device 200 is cooled down is, no further nitrogen gas is formed and the oxygen content under the shell device becomes imperceptibly low is. Then, the shell device is removed, and after further cooling of the cooling chamber to a temperature below −140° C. the cooling system can be put into operation as store for samples.

During normal cooling, the first cooling device is continuously filled up with liquid nitrogen, which volatilizes and maintains the nitrogen atmosphere in the cooling chamber. The nitrogen atmosphere has a horizontally graded temperature in the cooling chamber, which is −190° C. in the floor area at and −140° C. in the ceiling area. The dry, cool nitrogen gas is pressed from the cooling chamber into the upper operation rooms, and then discharged from there to the environment. Storing and destocking of samples is performed automatically during normal cooling. If undesirable ice accumulation is detected with cameras in the cooling chamber, which is indicative of leakage in the side wall, the leak is sealed, e.g. by pressing in a liquid, which freezes in the leak.

The technical check comprises testing of sensors, cameras and supply elements of the cooling system. In particular for testing the sensors, liquid nitrogen is filled up after a phase of reduced cooling by the first cooling device and, the resulting change in temperature in the cooling chamber is tracked using the sensors.

For maintenance/repair work, the operator 3 steps into the cooling chamber (see FIG. 1). Since a cryobank is to be operated with uninterrupted cooling over decades, the temperature cannot be raised in the cooling chamber during maintenance/repair work. Therefore, the operator 3 wears a heated protective suit with its own gas and electric supply. Since the cooling chamber is free of oxygen, a further operator 4 wearing a protective suit is on stand-by in the upper operation room 400 for the safety of the operator 3 in the cooling chamber 100. Both operators 3, 4 stand in radio contact and are observed from the outside by a camera system or a third operator 5 wearing the protective suit. Mechanical rescue systems (rope winches) are activated and ready for use, the protective suits are connected with a rescue rope. The internal temperatures and the breathing air supply are detected in the protective suits by device of sensors and transmitted to the user and the external staff. In the event of falling below limit values, a state of average is recorded and, if necessary, an alarm is triggered.

Standby operation may be provided for as an alternative to normal cooling. In case of failure of cooling devices or lack of liquid nitrogen, the cooling chamber is kept cold as long as possible. Here, all devices, which are not required, are switched off. No inspection of the cooling chamber is performed. All openings are closed. The floor trough of the first cooling device is, if possible, filled up by connecting an additional liquid nitrogen reserve. The electric auxiliary cooling is activated. The standby operation mode may include that the temperature in the cooling chamber is raised for a certain time period (days, weeks or months) to −80° C. If limit values, such as the temperature in the cooling chamber 100, are exceeded in the standby operation mode, a state of average is recorded and, if necessary, an alarm is triggered.

The clearance of a sample stock in the cooling chamber comprises a predetermined sequence of measures. A temperature of between −50° C. and −80° C. is established in the upper operation room. The sample containers are automatically transferred into this room and deposited in deep-cooled transport containers. In order to prevent ice precipitation, they are then closed and transported away. If required, this process can be supported by operators wearing protective suits in the upper operation room.

2. State of Average

An average can occur in the cooling system as a result of at least of the following operating situations, which comprise a failure of the first or the second cooling device through a coolant supply problem and/or through a technical damage, a complete failure of all cooling devices with rapid increase of temperature, an operating fault of a protective suit of an operator, a power failure/electric short-circuit, a fire in the cooling system or the environment, an inrush of water and any unauthorized entry/criminal actions.

In case of power failure or electric short-circuit, nitrogen cooling would not be a major problem. Preferably, an uninterruptible power supply and emergency power supply devices are provided for. A fire in the cooling chamber itself can hardly occur. On the device floor as well, this is not possible as long as the rooms are without oxygen. A problem typically arises only when oxygen still penetrates into the rooms through the ventilation system in case of an average. If a fire then occurs, dry chemical extinguishers are provided for in the rooms of the cooling system. Furthermore, there are emergency switches in all rooms, so that any possible fire caused by an electric fault can easily be prevented. In case of fire outside, the fire department should merely ensure that the cooling chamber device, which must be designed leak-proof against water penetration, is cooled so that the walls cannot be attacked. They should have a fire protection coating on the outside. Unauthorized entry or criminal actions are detected by device of sensors (motion sensors, IR detectors) and cameras and, if required, an alarm is triggered with the alarm device 401 (see FIG. 1).

It depends on the duration and action of the respective operating situation whether in the concrete case a state of average is detected, in which an operator and/or samples are exposed in the cooling chamber to operating conditions, which differ from a predetermined normal state.

The effect of the failure of one or more cooling devices depends on which one of the cooling devices forms the main cooling system and the secondary safety cooling system in the cooling chamber. When the main cooling device comprises an electric cooling system (second cooling device in FIG. 1), this will result in heating of the cooling chamber within a few hours in case of power failure or any other malfunctions. As soon as a critical temperature of, for example, −138° C. is reached, the secondary safety cooling system (first cooling device in FIG. 1) must be put into operation. For this purpose, liquid nitrogen is pumped into the floor trough 210. The liquid nitrogen is supplied from a storage vessel outside the cooling system, e.g. from a nitrogen tanker. If, in contrast, the main cooling system is operated with liquid nitrogen and the secondary safety cooling system comprises an electric cooling, failure of the main cooling system, e.g. due to an interruption of the supply of liquid nitrogen, is less critical. As long as the floor trough 210 in the cooling chamber 100 contains liquid nitrogen, the operating temperature in the cooling chamber can be kept e.g. over days up to a week. Before the liquid nitrogen 220 completely vaporizes from the floor trough 210, the secondary safety cooling system is turned on.

A state of average can occur when the failure of the main cooling is permanent and cannot be compensated for by the secondary safety system and/or repair work is required on the main cooling or the secondary safety cooling system, which requires for the cooling chamber to be warmed up. Furthermore, a state of average can occur if all cooling devices, i.e. the main cooling and the secondary safety cooling system fail and the temperature in the cooling chamber 100 is likely to rise above −138° C. In this case, a evacuation of samples is required, as will be explained in the following with reference to FIGS. 2 and 3.

Figure 2:
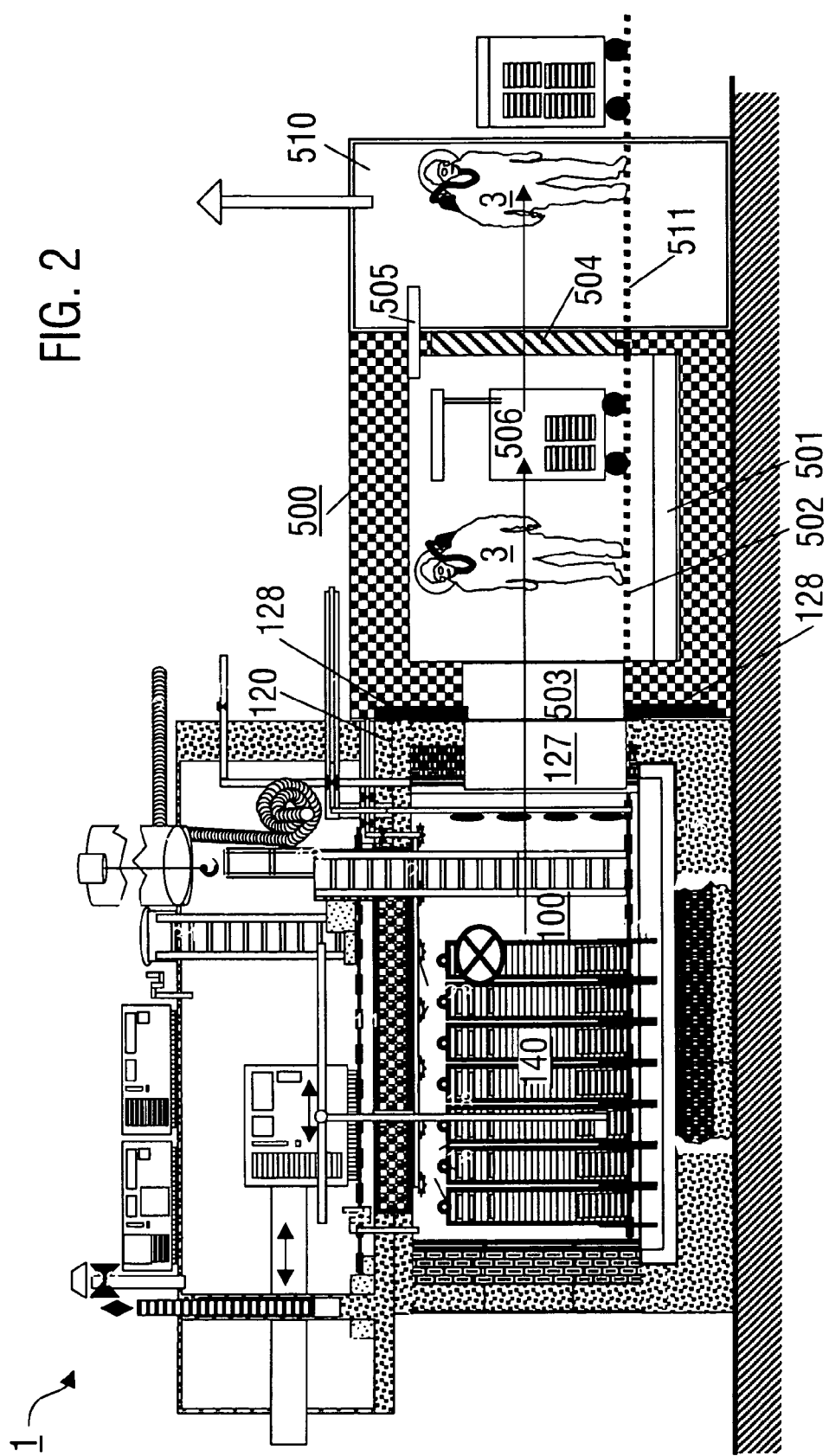
FIG. 2: a schematic cross sectional view of the cooling system according to FIG. 1 with a coupled evacuation container.

For evacuation of samples from the cooling chamber 100, an evacuation container 500 with an evacuation gate 510 is arranged on the docking device 128 on the external side of the side wall 120 (FIG. 2). The evacuation container 500 comprises a thermally insulated room unit, which is open towards the wall opening 127 with an opening 503 and contains a container trough 501 for receiving liquid nitrogen and a door 504. Above the container trough 501 is arranged a working platform 502, 511, which runs from the opening 503 through the evacuation container 500 and the door 504 into the evacuation gate 510. Between the evacuation container 500 and the evacuation gate 510 is a gas passage 505 provided for, through which nitrogen gas resulting in the evacuation container 500 is led out via the evacuation gate 510. This advantageously minimizes penetration of humid air, so that ice precipitations are prevented.

In case of an average, the evacuation of samples from the cooling chamber 100 comprises the following steps. At first, the evacuation container 500 is positioned on the external side of the side wall 120 and fixed and sealed on the docking device 128. Subsequently, the interior of the evacuation container 500 is cooled down. With liquid nitrogen in the container trough 501, a temperature below −50° C., in particular below −80° C., is adjusted. Subsequently, the wall opening 127 is formed by removal of the wall element 125 (see FIG. 1).

The evacuation of the samples then comprises the extraction of samples from the sample holding device 140 in the cooling chamber 100 and the transfer into a cryotank 506 (Dewar tank) capable of rolling. For this purpose, an operator 3 wearing the protective suit enters the evacuation container 500 via the evacuation gate 510 and the door 504 and the cooling chamber 100 through the wall opening 127. Advantageously, due to the tight coupling between the evacuation container 500 and the docking device 128, the evacuation of the samples can be temporarily interrupted. The wall opening 127 can e.g. be closed in order to continue the evacuation at a later point in time.

According to a variant of the invention, the evacuation container 500 can be fixedly connected with the external side of the side wall 120. In this case, advantages can result for the thermal insulation and gas-tightness of the connection between the cooling chamber 100 and the evacuation container 500.

The operating conditions in the cooling system can be such that the samples or an injured person must be removed instantaneously from the cooling chamber 100. This is e.g. the case if there is a risk of destruction of the samples in the cooling chamber by fire or mechanical action and/or an operator is injured in the cooling chamber. Since, in this case, the evacuation via the evacuation container 500 according to FIG. 2 can require too much time, quick recovery of operators and samples is alternatively to be made. During the quick recovery, samples and/or operators are removed from the cooling chamber 100 regardless of the icing but, however, while preserving the cooling of the samples.

Figure 3:
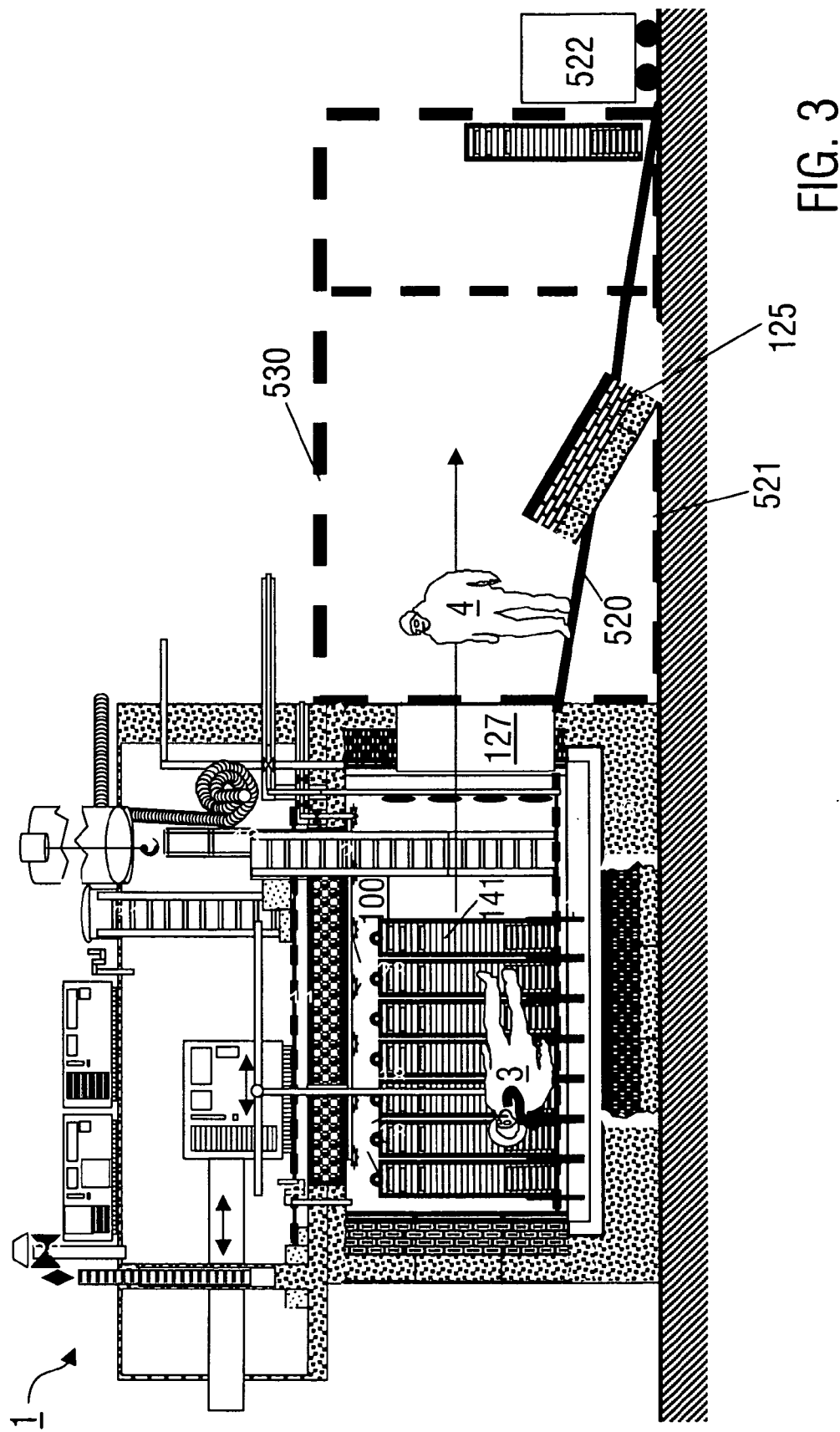
FIG. 3: a schematic cross-sectional view of the cooling system according to FIG. 1 with a ramp provided for evacuation of the cooling chamber.

For the quick recovery, a ramp 520 is arranged according to FIG. 3 on the external side of the side wall 120, which ramp leads from a bottom edge of the wall opening 127 in the side wall 120 to the floor 521 in the environment of the cooling system. The wall opening 127 and the ramp 520 can be enclosed by an evacuation gate 530. Through the evacuation gate 530, a locally dry and, if necessary, also cooled atmosphere can be provided in the environment of the wall opening 127. The evacuation takes place via the ramp 520 with the following steps.

After detection of the state of average, the ramp 520 is positioned on the external side of the side wall 120. The wall element 125 is removed so that the wall opening 127 is formed. The removal of the wall element 125 can be effected by manual action, with a mechanical tool or by device of directional blasting. The action with the mechanical tool can comprise e.g. cutting-out or mechanical pressing-out.

A helper 4, who wears a protective suit, can enter the cooling chamber 100 through the wall opening 127 in order to remove the injured operator 3 and/or the shelves 141 with the samples from the cooling chamber 100 via the ramp 520. From of the ramp 520, the samples are transferred into a ready cryotank 522 where the samples are secured. If the cooling chamber 100 can be impinged with warm air in case of detection of the state of average, it is not required that the helper 4 uses a protective suit. In this case, it is sufficient if the helper 4 wears warm clothing and a face shield.

Figure 4:
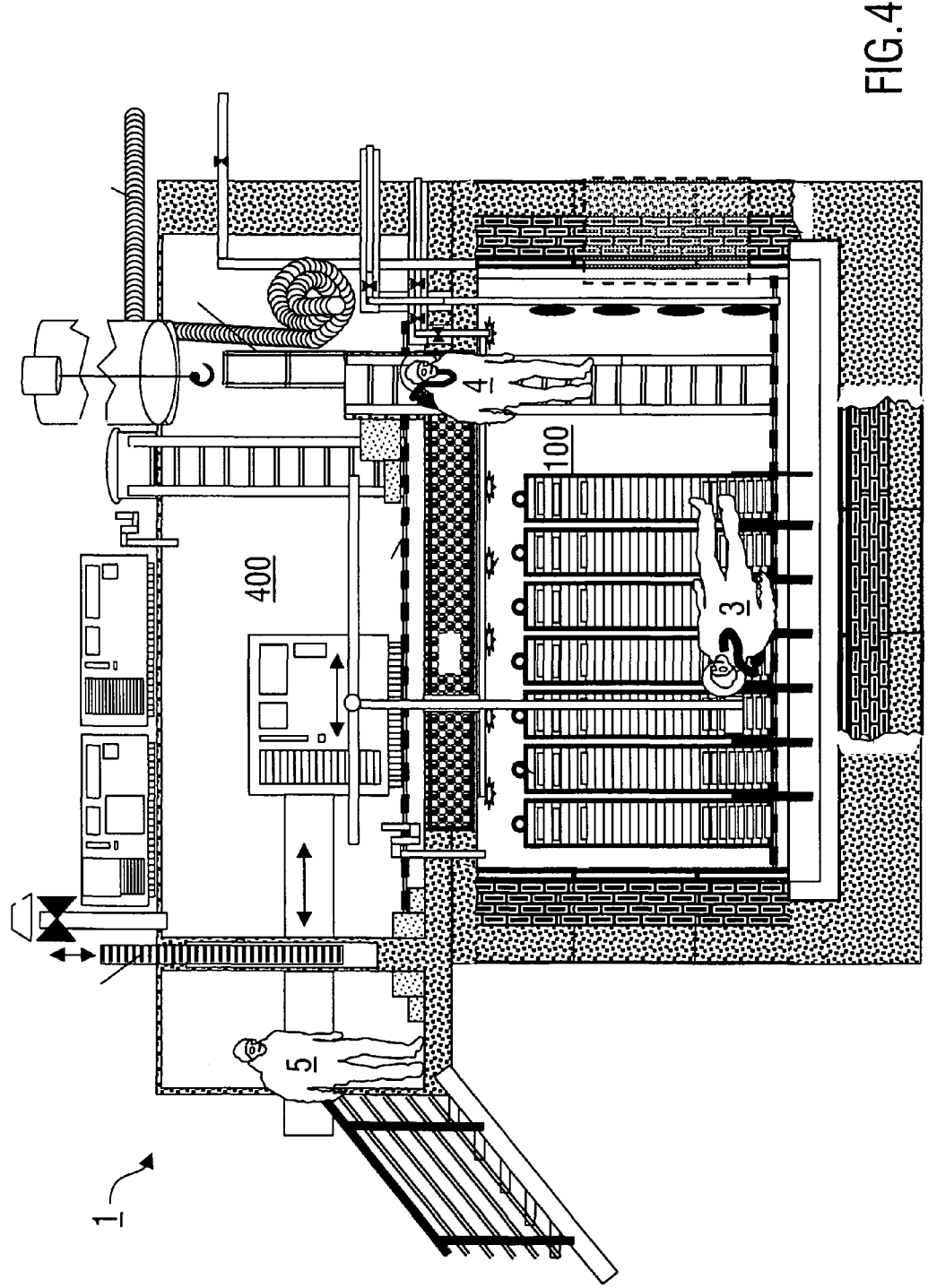
FIGS. 4 and 5: schematic cross-sectional views of the cooling system according to FIG. 1 with an illustration of the rescue process of an operator with a protection device shaped as a hood.
Figure 5:
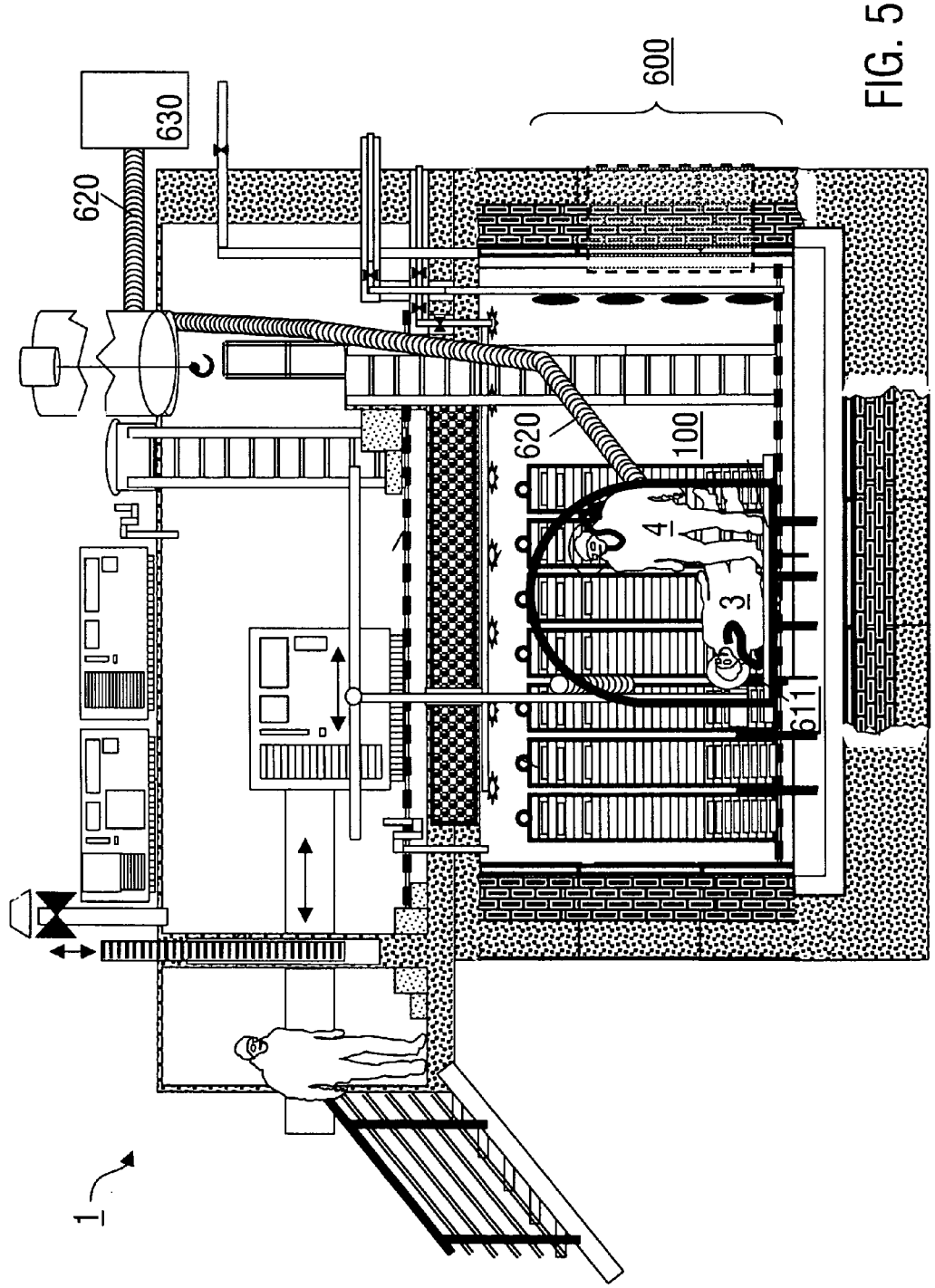

FIGS. 4 and 5 schematically illustrate the rescue of an operator 3 in the cooling chamber 100 using a protection device 600. For this variant of the invention, the protection device 600 comprises a hood 610, which is connected via a ventilation line 620 with an external ventilation system 630. The hood 610 is made of a material, which is flexible at the operating temperature in the cooling chamber, such as a metal foil. In the normal state of the cooling system, the hood 610 is in a folded-up state in the cooling chamber 100. In case of an average, the hood 610 can be unfolded by a helper 4 and used for protection of the injured operator 3 as is described in the following.

In the cooling chamber 100, an operator 3 can experience e.g. a faint, an injury or an adverse effect caused by an operating fault of the protective suit, light failure or an anxiety attack. The operator 3 lies in the floor area of the cooling chamber 100 without being able to help himself. When this state of average is detected, a first helper 4 descends from the operation room 400 via a ladder into the cooling chamber 100, while a second helper 5 is available for safety.

At first, the first helper 4 determines the cause of the state of average. The degree the limitation of the operator 3 is transmitted to the second helper 5 and, if necessary, further helpers outside the cooling system. If the state of average is caused by an operating fault of the protective suit of the operator 3, the helper 4 can temporarily couple the supply unit of his own protective suit with the protective suit of the operator 3.

If the operator 3 is in danger of life, e.g. due to the failure of essential functions of the protective suit, the unfavorable operating conditions in the cooling chamber 100 must immediately, e.g. within a minute, be changed as far as providing breathing air and increasing the temperature are concerned. For this purpose, the hood 610 is used. The helper 4 spreads the hood 610 over the operator 3. If available, an insulating mat 611 can be spread out prior to this on the floor area in order to simplify the creation of a local atmosphere. The hood 610 is coupled via the ventilation line 620 to the external ventilation system 630. This contains a ventilator and a heating device. Warmed-up breathing air is blown with the external ventilation system 630 into the interior of the hood 610. In case of high air throughput, the local atmosphere warms up so rapidly that use of the protective suit can be dispensed of for the operator 3. When using dry air, no mist occurs, and the protective helmet of the operator 3 can be opened.

If the operator 3 is capable of moving after a recovery, he can leave the cooling chamber 100 using the ladder after having worn the protective suit again. If, in contrast, the operator 3 is not capable of moving, the operator 3 remains at first under the hood 610 until further helpers can be present in the cooling chamber 100 in order to carry out evacuation through the ceiling opening, if necessary using the rope hoist 151.

Figure 6:
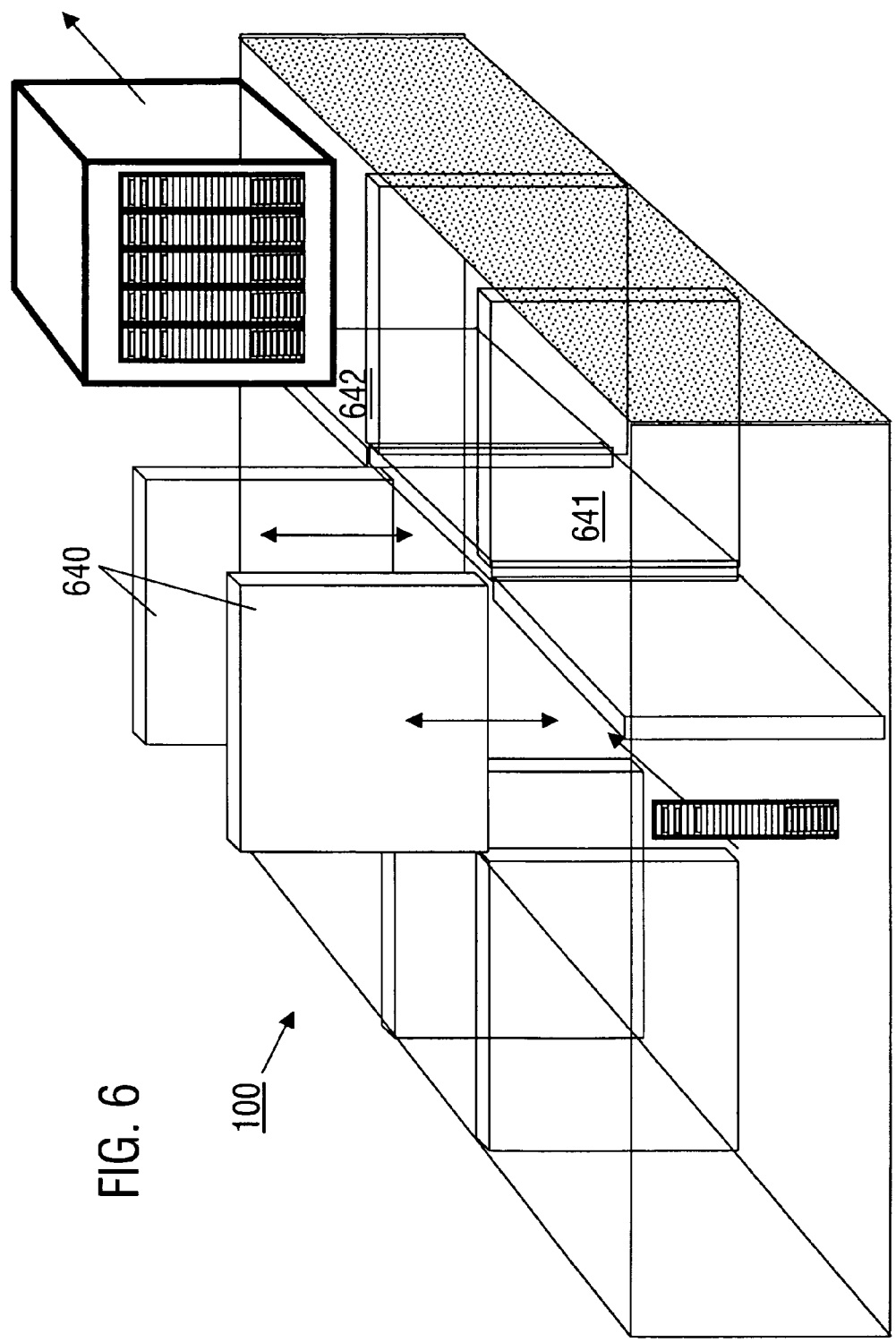
FIG. 6: a schematic perspective view of a cooling chamber with shiftable walls for the formation of a protection device shaped as a chamber.

According to a modified variant of the invention, the protection device can comprise shiftable partition walls 640 for creating a local protective atmosphere in the cooling chamber 100, as is illustrated schematically in FIG. 6. The cooling chamber 100 is provided with a system of partition walls 640, which can be inserted from above, e.g. from the operations room 400 (see FIG. 1), into the cooling chamber 100. With the partition walls 640, individual chambers 641 can be formed, which can be coupled via a ventilation line to an external ventilation system (not shown).

The segmentation of the cooling chamber 100 by device of the partition walls 640 also allows a simplified evacuation of samples from the cooling chamber 100. For example, it can be provided for that, with the partition walls 640, areas such as the chamber 642 are separated in a thermally insulated manner from the remaining cooling chamber 100. Subsequently, samples can be evacuated from the separate areas by lifting out, e.g. through the ceiling opening 131 (see FIG. 1). In the case of cooling chamber systems with a plurality of cooling chambers arranged the one behind the other or the one around the other, the samples can be shifted horizontally in a quick and easy manner as a shelf or individually while pulling up and lowering of the partition walls 640 is done until the samples are in the chamber 642. The total evacuation can then be carried out from the chamber 642, which can e.g. be removed completely with the samples (lifted out, shifted, transported away).

Figure 7:
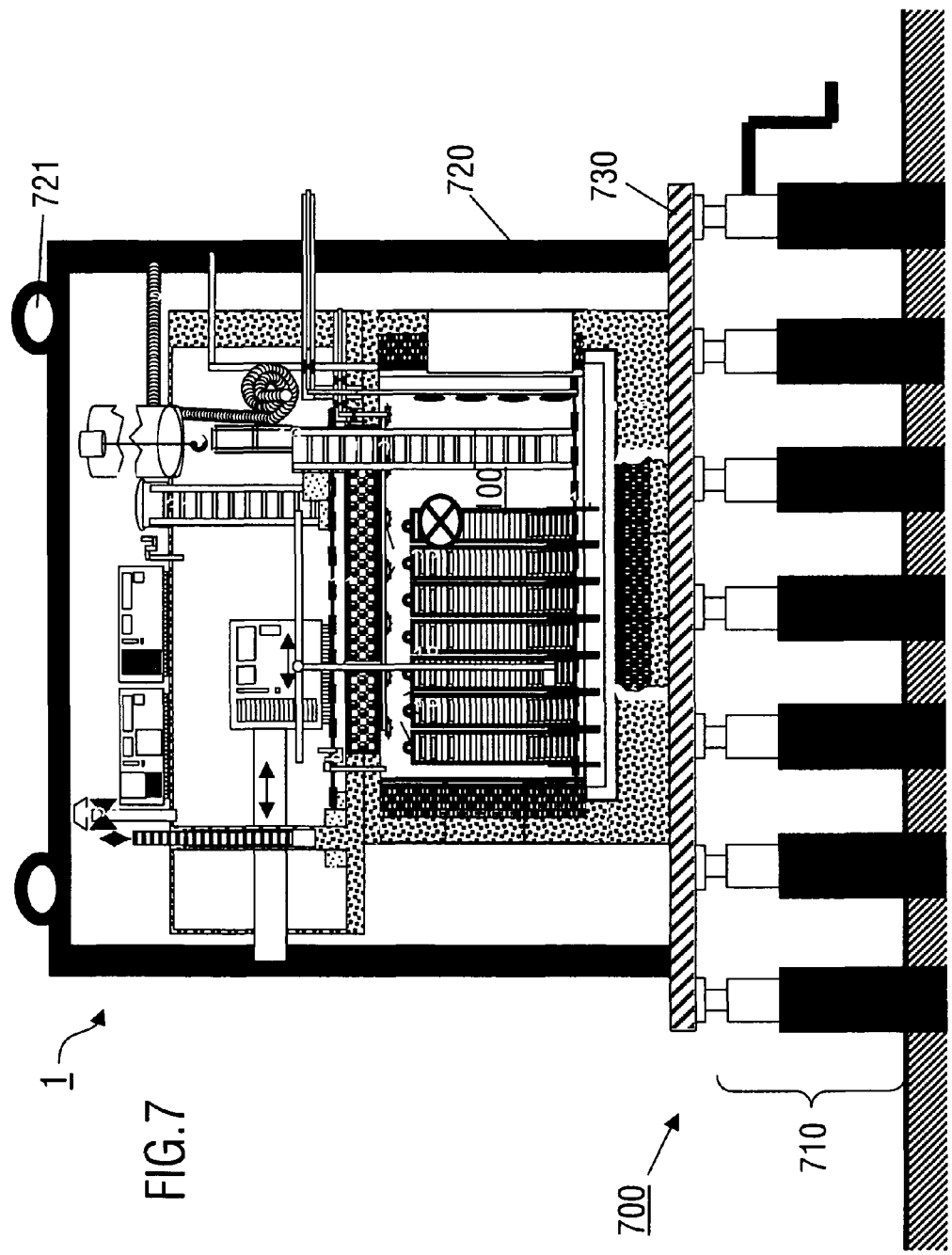
FIG. 7: a schematic cross-sectional view of features of a lifting device provided for according to the invention.

FIG. 7 illustrates in a schematic sectional view a cooling system 1, which is provided with a lifting device 700. The cooling system 1 is fitted with a massive frame 720 and a base plate 730. With the lifting device 700, the operating height of the cooling chamber 100 can be changed, for example in order to protect the cooling system 1 against floods. The lifting device 700 comprises e.g. a hydraulically operated carrier 710 and/or a crane (not shown). The base plate 730 can be lifted with the hydraulically operated support 710. The frame 720 is provided with engaging elements 721, which allow lifting of the cooling system 1 with a crane.

Lifting of the cooling system 1 with the crane is preferred when the cooling system 1 has the dimensions of a standard transport container. Otherwise, lifting is performed with the hydraulically operated support 710, which is adapted for a lifting height in the range of e.g. 1 to 2 meters. Alternatively, lifting of parts of the cooling chamber, such as the chamber 642 (see FIG. 6), with the crane can be provided.

Figure 8:
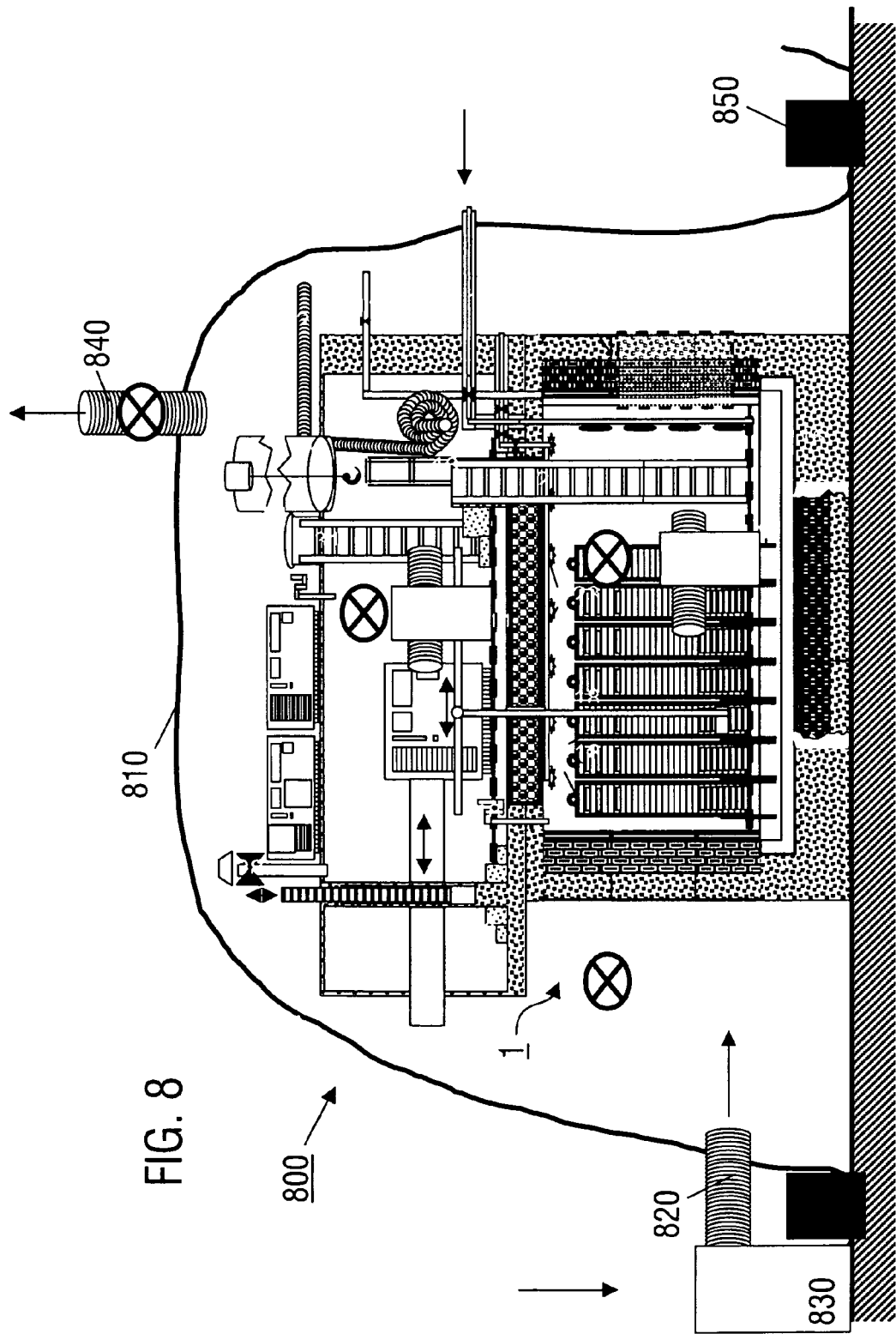
FIG. 8: a schematic cross-sectional view of features of a shell device provided for according to the invention.

FIG. 8 schematically illustrates a shell device 800 by device of which a system's protective atmosphere can be created. The shell device 800 is configured to impinge the whole cooling system with a protective atmosphere. The shell device 800 can e.g. provide protection against water penetrating from above and/or other weather phenomena.

The shell device 800 comprises a gas-tight, flexible foil 810, which connected via an air supply 820 with a ventilation device 830 and is fixed with fixing elements 850 on the floor in the environment of the cooling system 1. Supplied air can flow out through an air outlet 840. The foil 810 consists e.g. of plastics, such as polyolefin (like polyethylene), polypropylene or polycarbonate, as a single layer or as a multilayer composite foil.

The features of the invention which are disclosed in the above description, the claims and the drawings may be important both individually and in combination for implementing the invention in its various designs.

The invention claimed is:

1. A cooling system for cryopreservation of biological samples, comprising:
   a cooling chamber, which is delighted by a floor area, side walls and a ceiling area,
   a protection device, wherein the protection device is in the cooling chamber is configured for creating a local protective atmosphere in a environment of an operator, and comprises: (a) a hood which is movable in the cooling chamber, or (b) movable partition walls, which are shiftable in the cooling chamber, and with which a chamber can be created in the cooling chamber;
   an external ventilation system for impingement of an interior of the hood or an interior of the chamber with heated air, and
   a cooling device, which is provided for cooling of the cooling chamber with liquid nitrogen, wherein at least one of the side walls contains at least one predetermined wall element, that is a subregion of the at least one of the side walls and that is movable relative to the at least one of the side walls such that a wall opening can be formed in the at least one of the side walls.

2. The cooling system according to claim 1, in which the at least one predetermined wall element has at least one feature selected from the group consisting of
the at least one predetermined wall element is a detachable wall module of the at least one of the side walls,
the at least one predetermined wall element is shiftable perpendicular to the at least one of the side walls,
the at least one predetermined wall element can be manually moved by an operator, and
the at least one predetermined wall element can be separated from the at least one of the side walls.

3. The cooling system according to claim 1, in which are provided on an external side of the at least one of the side walls with the at least one wall element at least one of
a docking device for an evacuation container, and
a ramp, which falls off from a bottom edge of the wall element or the wall opening onto a floor in surroundings of the cooling system.

4. The cooling system according to claim 3, in which
the docking device is configured for a thermally insulated and gas-tight connection of the cooling chamber with the evacuation container with regard to an environment of the cooling system.

5. The cooling system according to claim 1, in which
an alarm device, which is configured for generating an alarm in reaction to any undesirable access to an interior of the cooling chamber, is provided for in the cooling chamber.

6. The cooling system according to claim 1, in which
the protection device comprises the hood, and the external ventilation system is arranged
for impingement of the interior of the hood with heated air.

7. The cooling system according to claim 1, in which
the protection device comprises the movable partition walls, and
external ventilation system is arranged for impingement of the interior of the chamber with heated air.

8. The cooling system according to claim 1 in which
the protection device is provided with an insulating mat with which the operator can be thermally insulated against the floor area.

9. The cooling system according to claim 1, which comprises
a lifting device, which is arranged for changing an operating height of the cooling chamber or of parts of it relative to a floor in an environment of the cooling system.

10. The cooling system according to claim 9, in which
the lifting device comprises at least one of a crane and a hydraulically operated carrier.

11. The cooling system according to claim 1, further comprising
a shell device, which is configured for creating a system's protective atmosphere, which surrounds the cooling system.

12. A method for operating a cooling system according to claim 1, comprising the steps of:
detecting an emergency state of the cooling system in which at least one of an operator and samples are exposed in the cooling chamber to operating conditions, which differ from a predetermined normal state, and
changing a state of at least one of the operator and the samples in order to expose the at least one of the operator and the samples to operating conditions, which are equivalent to the predetermined normal state.

13. The method according to claim 12, in which the step of changing the state comprises at least one of the steps of
forming the wall opening in at least one of the side walls and evacuation of at least one of the operator and the samples through the wall opening from the cooling chamber,
creating the local protective atmosphere in the environment of the operator in the cooling chamber with the protection device,
changing an operating height of the cooling chamber or of parts of it relative to a floor in an environment of the cooling system using a lifting device, and
creating a system's protective atmosphere, which surrounds the cooling system; with a shell device.

14. The method according to claim 13, in which the forming step comprises:
transporting the samples through the wall opening into evacuation container using a Dewar flask.

15. The method according to claim 13, in which the step of creating the local protective atmosphere comprises:
covering the operator with the hood, or formation of the chamber in which the operator is accommodated, and
impingement of the interior of the hood or the chamber with heated air.

16. The method according to claim 13, in which
the operating height of the cooling chamber is changed with at least one of a crane and a hydraulically operated carrier.

17. The method according to claim 13, in which the step of creating the system's protective atmosphere comprises:
covering the cooling system with a gas-tight foil, and
impingement of the space covered by the gas-tight foil with air.

* * * * *